United States Patent [19]
Moss

[11] Patent Number: 5,920,005
[45] Date of Patent: Jul. 6, 1999

[54] GEOSYNTHETIC LINER TESTING APPARATUS AND METHOD

[76] Inventor: Arthur L. Moss, 1238 Island Dr., Logan, Utah 84321

[21] Appl. No.: 09/127,172

[22] Filed: Jul. 31, 1998

Related U.S. Application Data

[60] Provisional application No. 60/054,567, Aug. 1, 1997.

[51] Int. Cl.$^6$ ..................................... G01N 3/56
[52] U.S. Cl. ............................................. 73/9
[58] Field of Search ................... 73/866, 9, 841, 73/843, 10

[56] References Cited

U.S. PATENT DOCUMENTS

| | | | |
|---|---|---|---|
| 3,552,195 | 1/1971 | Koprowski | 73/101 |
| 3,561,259 | 2/1971 | Barendse | 73/84 |
| 4,311,036 | 1/1982 | Kajdas et al. | 73/10 |
| 4,411,160 | 10/1983 | Lutenegger et al. | 73/843 |
| 4,559,812 | 12/1985 | Kitchen | 73/59 |
| 5,542,281 | 8/1996 | Lee et al. | 73/9 |
| 5,616,399 | 4/1997 | Theisen . | |

Primary Examiner—Robert Raevis
Attorney, Agent, or Firm—Madson & Metcalf

[57] ABSTRACT

A cylindrical, direct shear apparatus and method engage multiple layers of geosynthetic, geotechnical, or both types of materials for evaluating interface friction. Geosynthetic fabrics, geomembranes, naturally occurring materials (soils, rock, gravel, aggregate, other geotechnical materials), and the like maintain frictional contact in many applications. Conventional testing, as per ASTM standard D 5321-92 requires a comparatively modest displacement. Behaviors of geosynthetic membranes and geosynthetic fabrics may change substantially when displaced beyond the dimensions tested under ASTM standards. Accordingly, an apparatus for providing virtually unlimited displacement of layers under "normal" loading for establishing effective "displacement force" in order to establish an "effective coefficient of friction" over a range of displacements. The apparatus and method may rely on a standard, ASTM D-5321 width of sample, but is not restricted to the transverse displacement limitations in an orthogonal direction during the test. The cylindrical, direct shear apparatus and method are consistent with the operational parameters and instrumentation sensitivities required by ASTM D-5321.

30 Claims, 12 Drawing Sheets

GEOSYNTHETIC LINER TESTING APPARATUS AND METHOD

RELATED APPLICATIONS

This application is a continuation-in-part of a co-pending application, Ser. No. 60/054,567, filed on Aug. 1, 1997 and directed to a CYLINDER SURFACE SHEAR TEST APPARATUS.

BACKGROUND

1. The Field of the Invention

This invention relates to geotechnical sealing materials and, more particularly, to novel systems and methods for reliable testing of shear testing properties of geotechnical materials and geotechnical synthetics.

2. The Background Art

The term "geosynthetics" is used to describe a broad group of flexible construction materials that include geotextiles, geogrids, geonets, geomembranes, and geosynthetic clay liners. These materials are used in various civil engineering applications for separation, filtration, reinforcement, transmission, stress adsorption, and barrier functions.

Geosynthetics that are commonly used for waste or fluid containment include geotextiles, geomembranes, geonets, and GCLs. Many waste or fluid containment structures are constructed of layers of geosynthetic materials or geosynthetics against natural soils or aggregates. As a result, the frictional properties between materials can become extremely important, especially if the structures are constructed on slopes.

The use of geosynthetics in geotechnical and environmental construction projects has dramatically increased in recent years as the advantages of the geosynthetic products have been demonstrated. The use of a manufactured sheet-type geosynthetic product is often in a layered system where the interface properties can become very important. The use of multi-layered geosynthetic liner systems for landfills is an important example. Construction of landfill liners and covers with moderate to steep slopes has raised concerns about stability against sliding. Due to their low friction angles, the interfacial shear strength properties of different geosynthetic interfaces are integral parameters for design.

Geotextiles are very versatile materials that can be used for separation, filtration, reinforcement, transmission usually in combination with a geonet, and as a barrier usually impregnated with asphalt or a similar waterproofing material. Geotextiles are classified by both their base polymer and structure. The most common base polymers for geotextiles are polypropylene and polyester. The two primary geotextile structures are woven and non-woven. The main distinction among various woven geotextiles is the type of yarn used. The most common yarn types are slit tape, monofilament, and fibrillated.

Geomembranes are very low permeability synthetic membrane liners or barriers used in civil engineering projects for fluid or waste containment. They are typically used for liquid or vapor barriers. They are used extensively in environmental engineering applications such as waste containment as part of a mandated liner system.

There are three categories of polymers that are used for geomembranes: thermoset elastomers, thermoplastics, and bituminous materials. The manufactured liners of primary interest for interface testing are the thermoplastic geomembranes since they are the most extensively utilized liners. The thermoplastic membranes include high density polyethylene (HDPE), low density polyethylene (LDPE), chlorinated polyethylene (CPE), chlorosulfonated polyethylene (CSPE), ethylene interpolymer alloy (EIA), and polyvinyl chloride (PVC). The HDPE liner material is the most frequently used liner.

Geosynthetic clay liners are factory fabricated rolls of bentonite placed between two geotextiles or bonded to a geomembrane using an adhesive. The GCL is considered to be a geocomposite since it is fabricated from a geosynthetic material and bentonite clay. The bentonite clay is the critical component of a GCL since it is the source of the very low hydraulic conductivity of the GCL. When exposed to water, the bentonite will adsorb the water and swell. The resulting hydrated GCL has a hydraulic conductivity in the vicinity of $1 \times 10^{-9}$ cm/sec. The carrier material for a GCL can be a woven or non-woven geotextile or a geomembrane, depending on the design and construction of the GCL.

Testing of GCLs in the hydrated condition requires a period of time (often 1 to 3 days) where the dry bentonite clay in the GCL is allowed to hydrate in the presence of water or other fluid, under a specified normal load, before testing. In the process of hydration, the bentonite adsorbs water and can expand to several times it's initial volume due to the adsorbed water. Testing of the hydrated GCLs requires first hydrating the sample, then testing. Some conventional direct shear machines are configured for hydration at a known normal load away from the test device, transferring the sample to the test device, and then performing the test. The preferred method is to hydrate the sample under a known load in the test device and perform the test without disturbing the sample. Some direct shear machines are configured to hydrate and test in the test device. The Cylinder Direct Shear can be used with either method.

The interest in peak and residual friction angles increased significantly due to the 1988 Kettleman Hills waste landfill slope failure, where a slope stability failure occurred in a hazardous waste landfill (27 m or 90 ft high) in which lateral displacements up to 10.6 m (35 feet), and vertical settlements of up to 4.2 m (14 feet) were measured (Mitchell, et al., 1990). Failure developed by sliding within the composite, multi-layered geosynthetic-compacted clay liner system under the hazardous waste fill. Several geosynthetic-geosynthetic and geomembrane-compacted clay liner interfaces were found to have low frictional resistance.

Investigations used small 2.8 inch shear boxes with a relative shear displacement of less than 0.3 inches and pullout box tests with larger relative shear displacements in excess of 3 inches. The testing revealed that a peak friction was typically encountered at a small relative displacement, followed by a decrease in friction with increasing displacement. Peak strengths occur at very small relative interface shear displacements. If such displacements are exceeded by deformations occurring during construction and placement, the residual interface shear strength behavior is actually unknown.

The residual strength of a geosynthetic interface is an important design parameter but various test methods have differing relative displacements. Residual shear strengths (or residual friction angles) have been reported for displacement of less than one cm for small direct shear test displacements of 7 to 10 cm or more for large direct shear and pullout tests, and greater than one m for some torsion ring tests. Reported friction properties vary widely with different materials, conditions, and test methods. What is needed is a repeatable, reliable method and apparatus for determining an interface friction angle for each interface representative of field conditions and materials. Each current method has advantages and disadvantages. The primary disadvantage with the direct shear test is the limited displacement available.

A 0.3 m direct shear device for testing geosynthetics has since been standardized since 1992 through the development of American Society for Testing and Materials (ASTM) Standard D-5321, Standard Test Method for Determining the Coefficient of Soil and Geosynthetic or Geosynthetic and Geosynthetic Friction by the Direct Shear Method.

The reported shear strength parameters are typically the peak shear strength and the shear strength at the end of the test, which is often called the residual shear strength. For many geosynthetic materials, the residual friction angle and residual shear strength varies with displacement, with the shear strength decreasing with increased displacement. As a result, shear strengths are often reported at a fixed displacement or percent deformation, without determining the final or true residual friction.

It should be emphasized that most of the available shear testing methods have a relatively small displacement range (typically from 0.3 inch up to 3 or 4 inches, while real world failures often measure displacements in ranges of feet and sometimes tens of feet. A test method that could duplicate this scale of displacement would provide more reliable and more believable shear strength test results.

BRIEF SUMMARY AND OBJECTS OF THE INVENTION

An apparatus and method in accordance with the invention provides a new shear strength test device to generate high quality geosynthetic interfacial friction data in a manner that eliminates some of the inherent limitations of other test methods. The new testing device may be consistent with a standard 0.3 m (12-inch) direct shear test, with a base material, typically a geomembrane sample, wrapped around and fastened to a cylinder, rather than being placed on a flat plane. The interface geosynthetic is then wrapped around the cylinder, secured to an anchor bar and rigidly attached to the support frame, and is then encased in a latex rubber triaxial cell membrane. The normal force applied to the test specimen is provided by a confining chamber that is pressurized in a manner similar to the methods used in conventional triaxial tests. Interface friction is determined between the inner cylinder (geomembrane) and the interface geosynthetic based on the torque required to turn the inner cylinder, and by measuring the amount of rotation (sample displacement) under the given normal force.

The new test apparatus or device may be referred to as a Cylinder Direct Shear, and provides unlimited continuous displacement, constant direction of displacement, large sample size, minimized boundary effects, a wide range of displacement rates, a wide range of normal stresses, and a consistency of testing results by allowing a single sample configuration to be tested under a variety of normal stresses and rates of shearing without disturbing the sample setup.

Geosynthetics that may be tested as interfaces include geomembranes against geomembranes, geotextiles against geomembranes, geomembranes against GCLs, and geotextiles against GCLs. Other interface testing includes other geosynthetics such as geogrids, geonets, and erosion control products against other geosynthetics, or various geosynthetics against geotechnical materials such as cohesive or cohesionless soils. Other shear testing includes internal shear strength of various geosynthetic composites such as GCLs, liner composites, or drainage composites. Individual tests have been conducted with interfacial displacements of up to 1 m, and total interfacial displacements of 3 to 4 m have been achieved for a series of tests on certain interface combinations. These large displacements are far greater than the 7 to 10 cm displacements typically produced by conventional linear testing, and provide the peak interfacial shear strength as well as a true residual shear strength.

In addition, the large displacements from the Cylinder Direct Shear are consistent with the direction of manufacturing of the geosynthetic, as opposed to ring shear testing, which provides large rotational displacements on a disk with a non-uniform horizontal displacement rate, small sample size, and non-uniform direction of testing. Another advantage of the Cylinder Direct Shear device is that the cost to build and instrument the apparatus is substantially less than for the conventional devices with limited displacement.

Consistent with the foregoing needs, and in accordance with the invention as embodied and broadly described herein, an apparatus and method are disclosed, in suitable detail to enable one of ordinary skill in the art to make and use the invention.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 13, is not intended to limit the scope of the invention. The scope of the invention is as broad as claimed herein. The illustrations are merely representative of certain, presently preferred embodiments of the invention. Those presently preferred embodiments of the invention will be best understood by reference to the drawings, wherein like parts are designated by like numerals throughout.

Those of ordinary skill in the art will, of course, appreciate that various modifications to the details of the Figures may easily be made without departing from the essential characteristics of the invention, as described in connection with these figures. Thus, the following description of the FIGS. 1–13 is intended only as an example, and simply illustrates certain presently preferred embodiments consistent with the invention as claimed herein.

Figure 1:
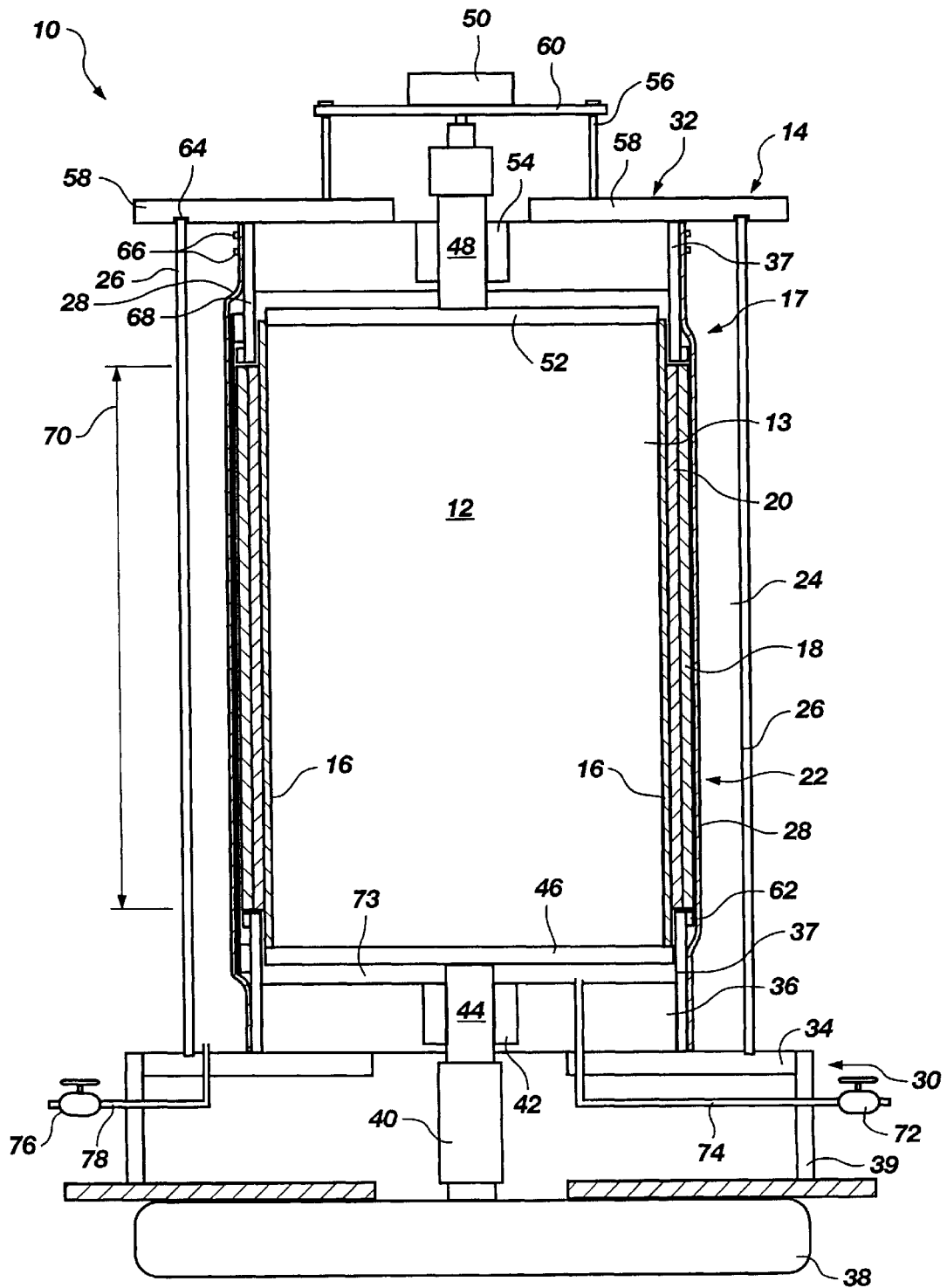
FIG. 1 is schematic, side, elevation view of an apparatus for implementing the invention.

Referring to FIG. 1, and referring generally to FIGS. 1–13, an apparatus 10 may include a drum 12 located within a sealable chamber 14. A base 16 or base layer 16 may effectively circumscribe the drum 12. A perimeter 18 or perimeter layer 18 may effectively cover the base layer 16. In one presently preferred embodiment, the drum 12 is a rotary member 12 adapted to rotate the base layer and other layers attached thereto. Nevertheless, the outermost frame 17 may be a rotary member with the drum 12 fixed. For manufacturing and operational simplicity, rotating the innermost member 12, the drum 12, is preferred.

In one embodiment, the perimeter 18 may be exposed directly to the chamber 14. In certain embodiments, the perimeter 18 is exposed to pressure in the chamber 14, the perimeter 18 or perimeter layer 18 being flexible and free to move in a radial direction toward the center of the drum 12.

In one presently preferred embodiment, an interface 20 or interface layer 20 contacts the base layer 16 and the perimeter layer 18. As a practical matter, the base 16 and the interface layer 20 may be the only layers of interest. Nevertheless, in other embodiments, a base layer fixed along an axial line to the drum 12 in order to move therewith, may contact the interface layer 20. Similarly, the perimeter layer 18, fixed along an axial line with respect to the frame 17, is restrained from moving in a circumferential direction. An interface layer 20 may contact both the base layer 16 and the perimeter layer 18. Alternatively, the base layer 16 and perimeter layer 18 may contact one another, rendering the perimeter layer 18, effectively, the interface material 20. Nevertheless, in many situations of interest, the relationship between a base layer 16 formed of one geosynthetic material, a perimeter layer 18 formed of another geosynthetic layer, may be tested for their performance in contact with a third interface layer 20 formed of one or more other naturally occurring or synthetic materials.

The chamber 14 encloses a pressurized region 24. The pressurized region, bounded by a wall 26, is preferably cylindrical in shape. Given the natural strength and equalization of stress in a hoop-stress configuration, the wall 26 may be optimized for strength, weight, size, thickness, and so forth, by using a cylindrical geometry.

Pressure applied to a surface represents stress. Stress is defined in units of force per unit area. Accordingly, pressure is stress. A membrane 28 sealed against the frame 17 to capture the entire drum 12 with its layers 16, 18, 20 therein, is fluid-resistant. That is, sealing the drum 12 and its appurtenances within the membrane 28, renders the membrane 28 a loading member 28 or stress member 28.

In one presently preferred embodiment, the membrane 28 seals fluid in the pressurized region 24 away from the layers 16, 17, 18. Therefore, the membrane 28 must transfer radially all stresses due to the pressurized region 24 acting in a radial direction upon the membrane 28. Uniform, hydrostatic pressure in the pressurized region 24 uniformly loads all areas of the base layer 16, perimeter layer 18, and any intermediate interface layers 20 uniformly and universally in a radial direction, while permitting radial non-uniformities within the outer most envelope thereof. That is, for example, a steel band, a segmented wall, or the like, may apply pressure to the stackup 22 nevertheless, rigid bodies are very difficult to maintain perfectly smooth or perfectly cylindrical. Thus, pressure in the pressurized region 24 can apply uniform pressure without regard to geometry, across the entire outer surface of the stackup 22.

In one presently preferred embodiment, a support 30 may include numerous members for supporting the chamber 14, the stackup 22 of layers 16, 18, 20 the drum 12, and so forth. A super structure 32 supports the pressures in the pressure chamber 24 as well as instrumentation, stability of the drum 12, and so forth. In one embodiment, the support 30 includes a frame 34 providing direct support to the chamber 14. Similarly, a frame 36, whether part of frame 34, or whether free standing elsewhere on the support 30, provides axial support to the stackup 22 materials.

The wall 37 supports radial pressure from the pressurized region 24, seals the membrane 28, supporting a portion of the membrane in a radial direction, supports the stackup 22 material layers 16, 18, 20 in an axial direction, and may support a seal 62 or sealing ring 62 for maintaining all loose (e.g. naturally occurring geotechnical materials such as soils, sands, etc.) within the stackup 22.

In one embodiment, a drive 38 may include various motive means and power transmission devices, for imparting a torque to the drum 12. The drive 38 is fixed with respect to the foundation of the structure 30, to remain rigid with respect to all of the structure 30, for all practical purposes. Nevertheless, the drive 38 does provide motive force or motive torque through a load cell 40 to the drum 12. The load cell 40 maintains torque at a particular, selected value, and may be operably connected to the drive 38 for feeding back data corresponding to the applied torque, effective to stabilize torque loads at a designated value. Meanwhile, the load cell 40 may provide output data indicating the actual torque as a function of time, position, and so forth to be used in analysis of data from the apparatus 10.

As a practical matter, bearings 42 may support a shaft 44 in a radial direction. In certain embodiments, the bearing 42 may also be a thrust bearing for imparting axial support (e.g. axial load to the shaft 44, thus supporting the turn table 46 of the drum 12.)

A shaft 48 disposed to correspond to the shaft 44, but extending at the opposite end of the drum 12, may be a separate shaft, a lug, or may actually be a part of the shaft 44. In one embodiment, a single shaft 44 may extend completely through a drum 12, and a drum 12 may be solid, or structurally hollow with struts, braces, and the like maintaining a surface 13 in a position to support the base layer 16. Thus, the shaft 44 and the shaft 48 may actually be a single shaft 44 extending axially along a radial centerline of the drum 12.

A sensor 50 may be operably connected to detect rotation of the shaft 48. The sensor 50 may use printed circuit resolvers, LVDT adaptations, mechanical distance measurement, counters, marks, laser reflection from bar codes, electrical inductants, or other suitable means for detecting position, velocity, and so forth of a surface of the shaft 48. In general, one objective of the sensor 50 is providing an angular displacement and angular velocity of the rotating member, typically the rotating drum 12. The sensor 50 may include any amount of integration of information. For example, a clock in the sensor 50 is not required, if the sensor 50 is connected to a computer or timer elsewhere for providing analysis algorithms. Nevertheless, the sensor 50 may provide all data collection, data integration, analysis processing, and display of important information.

A cap 52 may secure materials within a drum 12. That is in one embodiment, the drum may be hollow, providing only a surface 13 for supporting a base layer 16. Nevertheless, in certain alternative embodiments, the drum 12 may actually be a geotechnical material, such as a cohesive soil, non-cohesive soil, concrete, or other construction material. Accordingly, the cap 52 may actually form and contain the drum 12 of material.

Bearings 54 minimize friction while supporting the shaft 48 within the frame 58. As a practical matter, the bearings 54 need not be thrust bearings. In fact, if the bearings 42 are thrust bearings, then the bearings 54 should, in accordance with good engineering practice, slide freely. Moreover, the bearings 54 may be self-aligning to prevent binding, bending, and other results of residual, unbalanced forces. Likewise, the bearings 42 may be mounted to self-align with the shaft 44 and with the shaft 48 and bearings 54.

The sensor 50 or sensor suite 50 may mount to the frame 58 by means of an offset 56 or standoff 56 supporting a base 60. A certain selectivity in positioning is arbitrary. Nevertheless, the standoff 56 may effectively isolate the sensor system 50 from imparting spurious loads and tolerances in conflict with the bearings 54 supporting the shaft 48 within the upper support structure 32.

In one embodiment, a seal 62 seals materials within the stackup 22 from escaping about the wall 37. For example, in certain layups 22, naturally occurring materials may be disposed within or without restraining layers. Accordingly, mechanical and volumetric restraints on the stackup 22 may be embodied on the wall 37 and the seals 62.

Various seals 64 are disposed within the frame 34 and frame 58, sealing the wall 26 to form a region 24 capable of sealing pressure. Moreover, seals 66, such as 'O' ring seals, gaskets, and the like, may suitably serve as the seals 64 of the chamber 14. Likewise similar seals and 'O' rings 66 may seal the membrane 28 against the wall 37. One may note that the wall 37, as illustrated in FIG. 1, may be disjoint. An upper wall 37 and a lower wall 37 may directly connect to one another. On the other hand, other portions of the supporting structure 30 and super structure 32 may support the walls 37. The resulting sealing effect of the seals 66 renders the membrane 28 and the wall 37 a contiguous sealed surface with respect to a fluid captured within the pressure chamber 24. The seals 64 between the frames 34, 58 and the wall 26 render the pressurized region 24 a pressurized annulus when pressurized with fluid. An upper wall 68 is the same as the upper wall 37. Nevertheless, the wall 68 may be an independent wall.

A width 70 of a stackup 22 may conform to standards established by the American Society for Testing Materials (ASTM). For example, ASTM standard D 5321-92 specifies linear displacement testing for a coefficient of friction between soils and geosynthetics materials, or between geo-synthetic materials, by a direct shear method. Nevertheless, the ASTM standard, ASTM D 5321-92, provides only limited displacement. At displacements larger than those tested in the ASTM D 5321-92 test, failure or over design are likely, that is, comparatively small displacements do not tell the entire story needed for engineering design of geosynthetic layers in situ.

Nevertheless, a width 70 may be selected to correspond to the sample width required by ASTM D 5321-92. Nevertheless, due to the cylindrical configuration of the apparatus 10, and particularly the drum 12, the effective length, and the effective displacement of a base layer 16 with respect to a perimeter layer 18 is comparatively long, on the order of the circumference, and may actually be infinite for all practical purposes. That is, the drum 12 may continue rotating as long as the displacement of the base layer 16 with respect to the interface layer 20 and the perimeter layer 18 have meaning.

A valve 72 may open a conduit 74 leading from a chamber 73 to ambient. Meanwhile, a valve 76 connects a source of pressurized fluid (not shown) to a conduit 78 leading into the pressurized region 24. Accordingly, the source providing fluid through the valve 76 and the conduit 78 into the pressurizing region 24 sustains the pressure against the membrane 28 for loading the stackup 22. In one embodiment, the valve 72 may open a conduit 74 for evacuating pressure from the cavity 73 corresponding to the drum 12. During testing, the valve 72 may simply be left open in order to equalize pressure between an ambient and the cavity 73 containing the drum 12.

Figure 2:
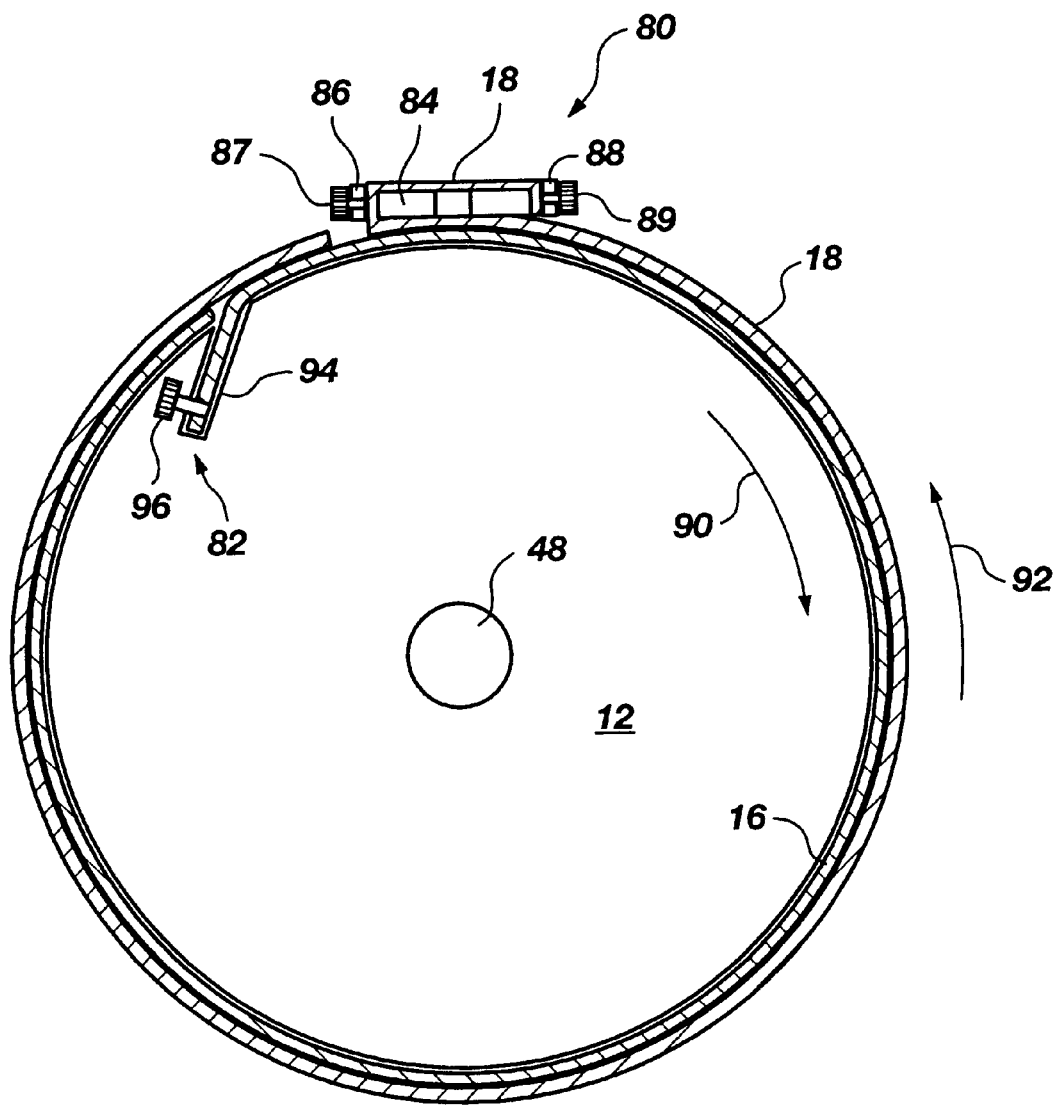
FIG. 2 is a top plan view of schematic representation of an apparatus in accordance with the invention.
Figure 3:
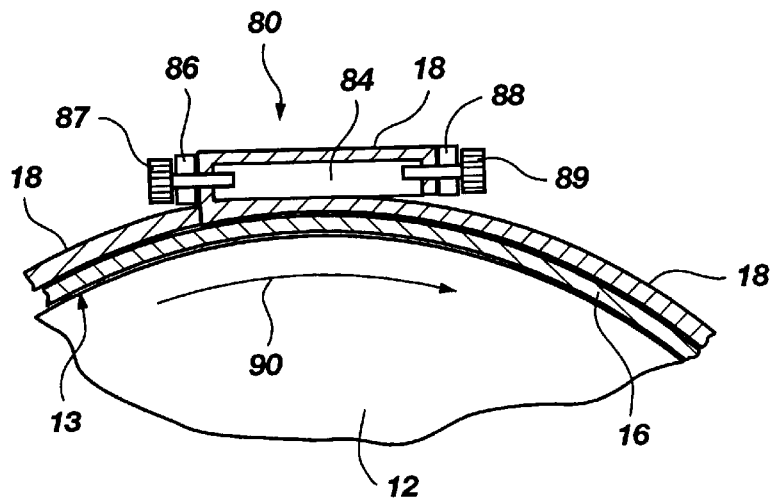
FIG. 3 is a schematic, top plan view of a cutaway portion of the apparatus of FIG. 1, illustrating a selected embodiment of a clamp for securing geosynthetic materials in the apparatus of FIG. 1.
Figure 4:
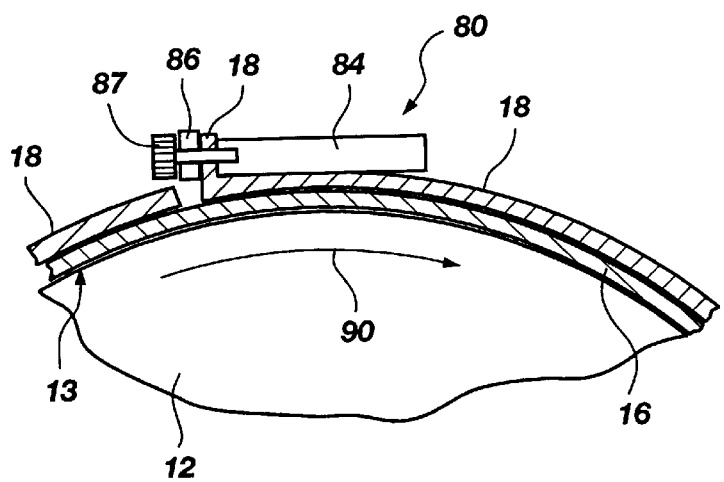
FIG. 4 is a schematic, top plan view of a cutaway portion of the apparatus of FIG. 1, illustrating a selected embodiment of a clamp for securing geosynthetic materials in the apparatus of FIG. 1.

Referring to FIGS. 2–4, a drum 12 needs to positively displace the base layer 16. Similarly the outer frame 17 needs to secure the perimeter layer 18. Again, the interface layer 20 may be associated with either the base layer 16, the perimeter layer 18, or may be free to move with either one 16, 18. Similarly, the interface layer 20 may actually include multiple layers. The importance of the effective friction factor is sometimes associated with specific individual layers 16, 18, 20 and their inter-relationship. Other times, the over all effect itself is important information, regardless of the particular constituents in the stackup 22. However, in general, knowledge of which layers 16, 18, 20 have the lowest shear strength is critical.

The clamps 80, or clamping assemblies 80 are important for securing the perimeter layer 18 to the frame 17. In general a clamp assembly 82 secures the base layer 16 to the drum 12.

In one presently preferred embodiment, a bar 84 or anvil 84 (alternatively referred to as a rack 84) is mounted in a structurally rigid relationship with the frame 17. A dog 86 or keeper 86 provides a distribution of force over the layer 18, wrapped around the bar 84. A screw 87 secures the dog 86 or keeper 86 against the anvil 84 or bar 84. Accordingly, a more-or-less even distribution of stress along an axial dimension 70 (width 70) near one edge of the perimeter layer 18 equalizes stress, minimizes opportunity for tearing, and provides a fixed datum for evaluating distortion or displacement of the material of the perimeter 18.

In one embodiment, an additional dog 88 or keeper 88 may be secured by an additional screw 89 (actually multiple screws penetrating through the keeper 88 along the axial width 70 of the perimeter layer 18) for securing the perimeter layer 18 against movement in the direction of rotation 90. Thus, the clamping assembly 80, by the basic support of the bar 84 fixed to the frame 17, imparts a resistance force 92 in opposition to the direction of rotation 90 of the base layer 16 about the rotating drum 12.

In the illustration in the FIG. 2, the direction of rotation is illustrated as a direction 90. Nevertheless, in certain embodiments, the direction of rotation may be opposite. However, by relying on the direction 90 of rotation, the slot 94 effectively pushes the base layer 16. To the extend that the base layer 16 is sufficiently thin or flexible that pushing will not work properly, the direction of rotation may be reversed. In such an event, the orientation of the clamping block 80 would be reversed to trail the perimeter layer 18 tangentially in an opposite direction therefrom.

The slot 94 of the clamping mechanism 82 may include a keeper 86 and set screws 96 for capturing the base layer 16 within the slot 94. Nevertheless, since the direction of rotation 90 tends to drive the base layer 16 further into the slot 94, the set screws 96 serve primarily to maintain orientation and limit distortion, along an axial length (e.g. the width 70) of the base layer 16 and the drum 12.

Referring to FIG. 3, the details of a clamping block 80 illustrate that the perimeter material 18 may actually lap itself coming under the material (between the clamp mechanism 80 and the drum 12, with respect to the portion of the perimeter material 18 wrapped around the block 84).

Referring to FIG. 4, in one embodiment, the perimeter material 18 may actually not completely wrap itself around the drum 12. In the embodiment of FIG. 4, a particularly thick and stiff perimeter material 18 may merely make a single turn about the block 84.

Figure 5:
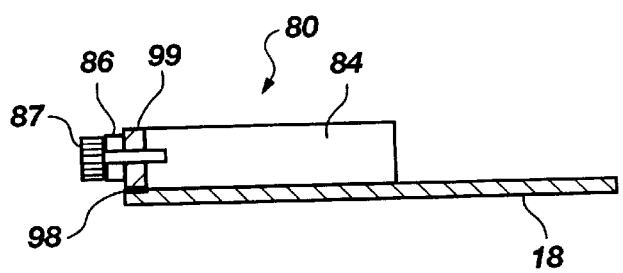
FIG. 5 is a schematic, top plan view of a cutaway portion of the apparatus of FIG. 1, illustrating a selected embodiment of a clamp for securing geosynthetic materials in the apparatus of FIG. 1.

Referring to FIG. 5, the perimeter material 18 may actually require a weld 98, preferably fully penetrating and thermally welded from both sides of the material 18. In one embodiment, a spur 99 is secured by a weld 98. Welding may be done by applying heat. In one embodiment, the block 84 may be adapted to have a radius for curving the perimeter material 18 sufficiently to be engaged by the keeper 86 and the capturing screw 87.

Figure 6:
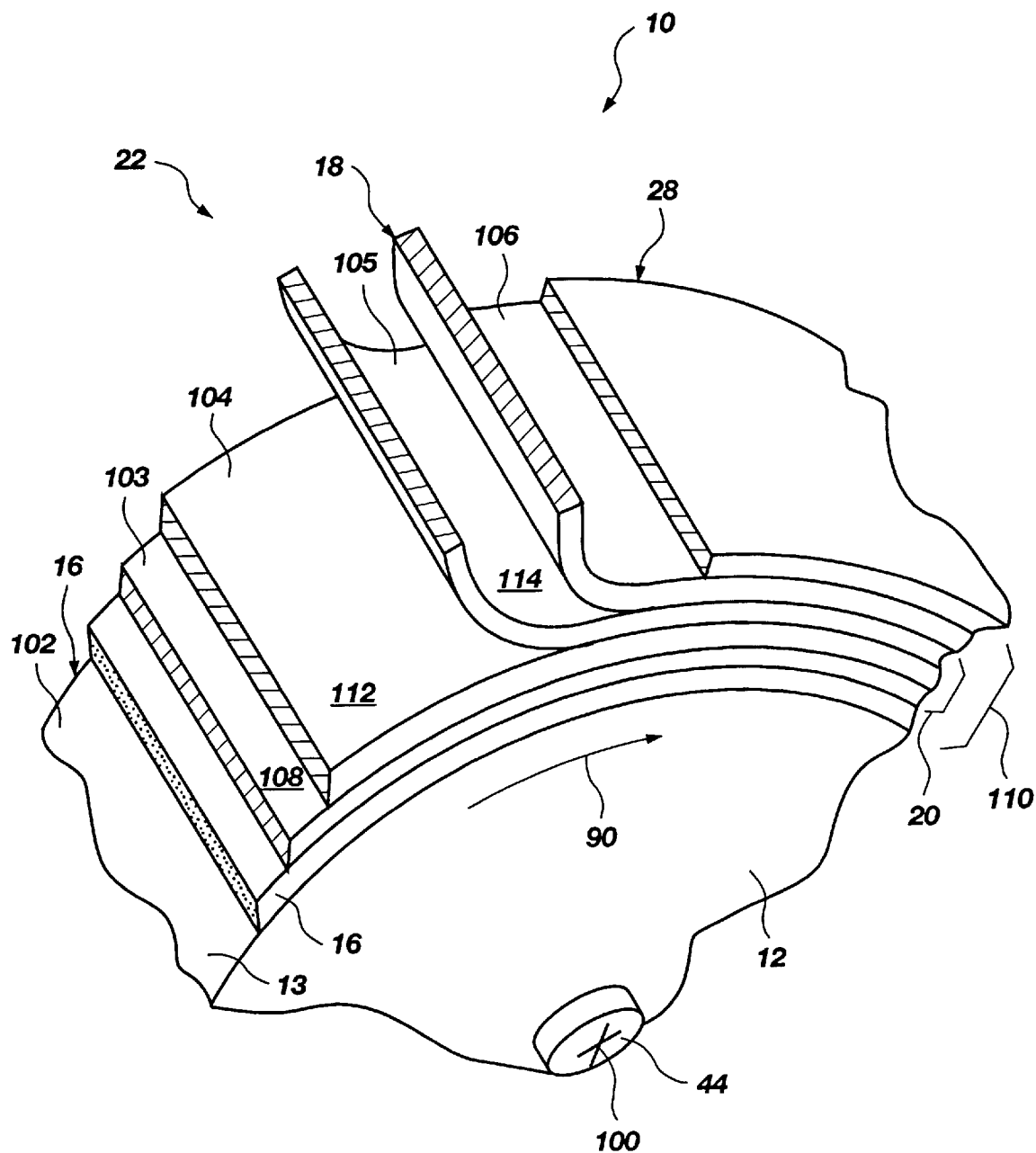
FIG. 6 is a perspective, cutaway, cross-sectioned view of a schematic representation of a layup of various materials for testing in the apparatus of FIG. 1.

Referring to FIG. 6, various optional layers may be stacked up between a frame 17 and a drum 12. The drum 12 rotates in a direction 90 about a centerline 100 or center of rotation 100, typically within the shaft 44. In one presently preferred embodiment, the surface 13 of the drum 12 may be metallic. In other embodiments, the surface 13 may be a geotechnical, naturally occurring construction material, such as a cohesive soil, non-cohesive soil, or the like. The pressurizing membrane 28 seals and loads the stackup 22 of the apparatus 10.

In one presently preferred embodiment, the various surfaces 102, 103, 104, 105, 106 interface the individual layers 16, 18, 108, 112, 114 as well as the membrane 28. As a practical matter, the surface 106 does not experience friction. That is, the perimeter layer 18 is fixed with respect to the frame 13 to remain stationary therewith. Accordingly, the surface 106 experiences only a pressure load from the pressurizing region 24 of the chamber 14.

The particular types of geosynthetic materials and geotechnical materials available are growing. Nevertheless, typical for the base layer 16 is a geomembrane of high density polyethylene (HDPE), and typical for a layer 108 may be a wrapped clay material, such as a dry, hydratable clay secured between layers of a geotextile material. A layer 112 may be a texturized geosynthetic membrane such as a highly pitted or ridged, solid polymeric layer for sealing, yet engaging materials. The layer 114 may be a naturally occurring material of some selected thickness. Alternatively, a geotextile for engaging a ridged surface 104 of the layer 112 may be used. Thus, the layer 114 may actually be fixed to the perimeter layer 18, in that the perimeter layer 18 may be a smooth layer for simply providing support to the layer 114. Alternatively, the layer 114 may be free to engage or slip with respect to the layer 18, in any particular test. Similarly, the layer 114 may actually be a loose material or a cohesive soil, or other naturally occurring material to be tested. In general, the stackup 110 exists primarily to test the interface layer 20 which may be comprised of one or more layers of one or more materials. In one embodiment, the interface layer 20 is nonexistent. The base layer 16 is one layer, the perimeter layer 18 is another material, and the interface therebetween is the subject of interest. In other embodiments, various layups 110 may be created. In another embodiment, the perimeter layer 18 may be the only layer, and the drum 12 may be a cylindrical sample of a compacted, naturally occurring soil sample.

Figure 7:
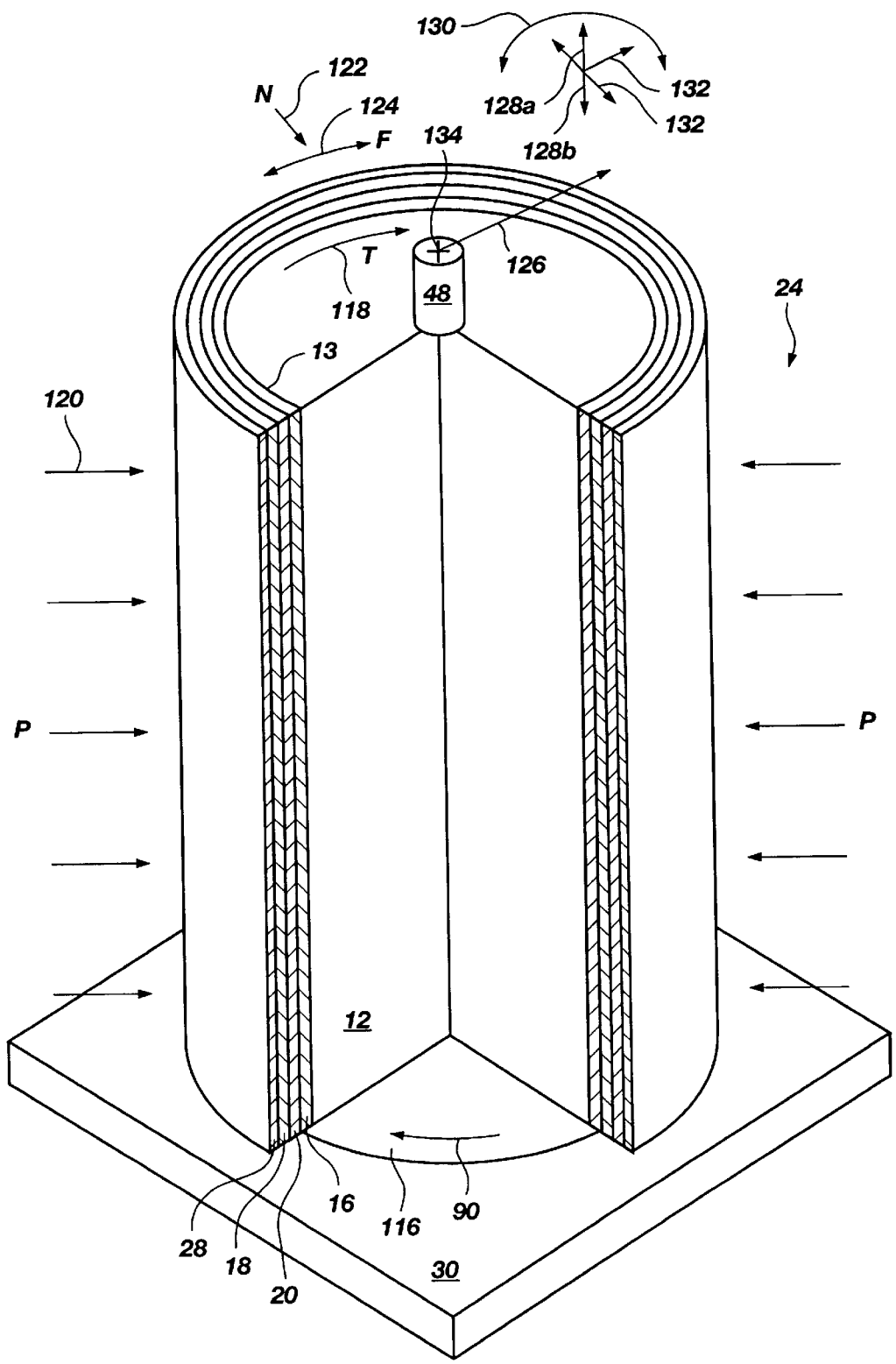
FIG. 7 is a schematic, perspective, partially-cutaway, cross-sectional view of one embodiment of a cylinder and layup for testing geosynthetic materials, with or without geotechnical materials, in accordance with the invention.

Referring to FIG. 7, a schematic illustration of the apparatus of FIG. 1 reveals a turn table 116 corresponding to the table 46 of FIG. 1. The drum 12 is configured to rotate with the table 116 in the direction 90, imparting a torque 118 to the apparatus 10, about the shaft 48, rotating about a center of rotation 134. In general, a pressure 120 in the pressurized region 24 of the chamber 14 imparts a normal force 122 uniformly against the membrane 28, loading the perimeter layer 18. A force 124 transmitted between individual layers 16, 18, 20 eventually accommodates the full torque 118 required by the shaft 48 to rotate the drum 12. The resistance force 124 will operate counter to the direction of rotation 90.

In general, a radius 126 at which a resistance force 124 occurs figures into the torque calculation. In general, the axis of rotation 134 or centerline 134 about which the drum 12 rotates is an axial direction 128, in which 128*a* is up and 128*b* is downwardly. A circumferential direction 130 or tangential direction 130 is orthogonal to the axis 134 of rotation, and the radius 126. The circumferential or tangential direction 130 corresponds to the options for the direction 90 of rotation of the turn table 116 and the drum 12.

The radial directions 132 are various, but are always outward from the center of rotation 134 or axis 134.

Figure 8:
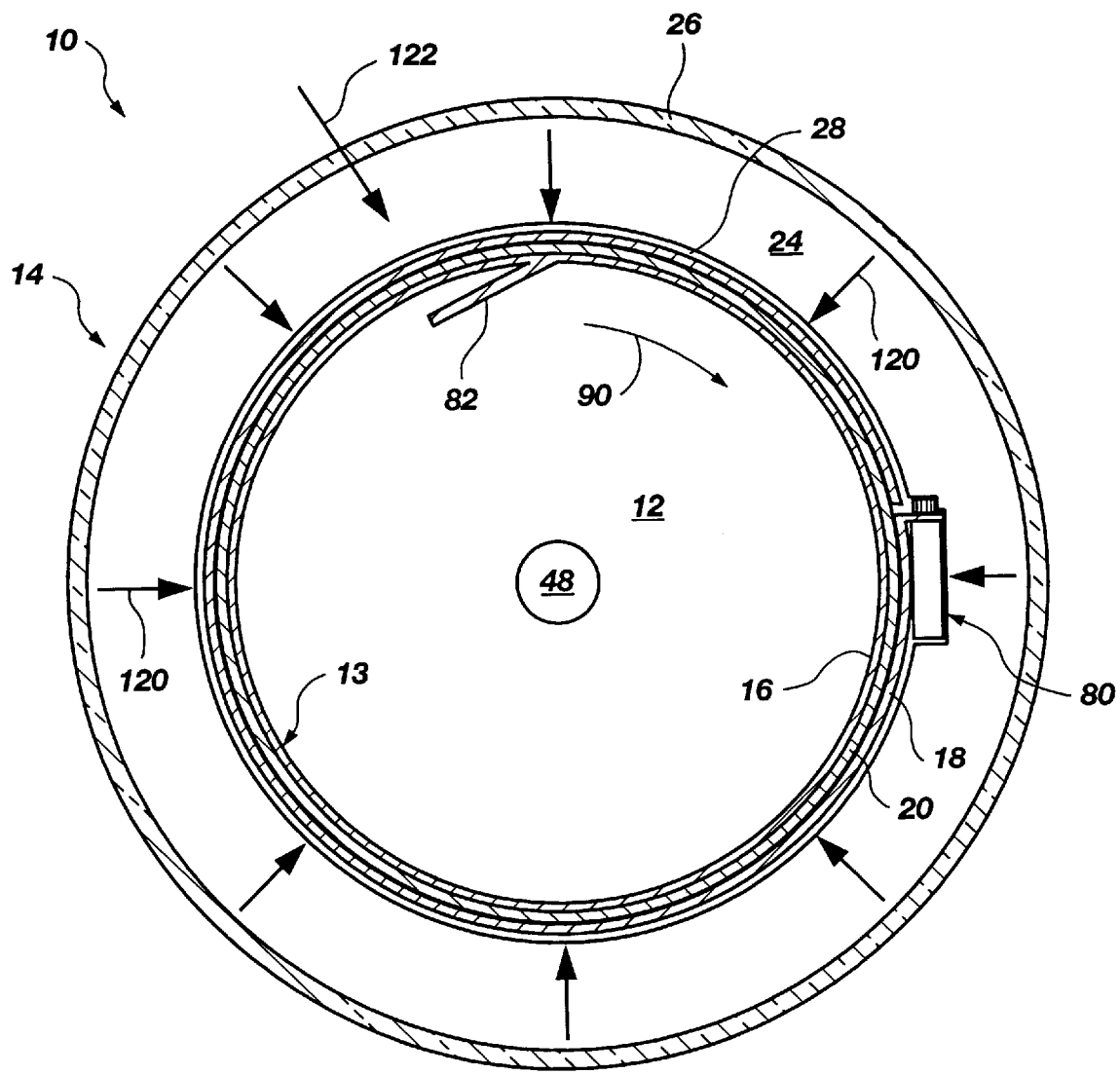
FIG. 8 is a schematic, top plan view of one embodiment of the apparatus of FIG. 1.

Referring to FIG. 8, a schematic illustration of the apparatus of FIG. 1, in a top plan view demonstrates the functional relationship between the shaft 48 rotating a drum 12 in a direction 90. The base layer 16 is driven into the slot 82, but is prevented from buckling due to the inherent stiffness properties of the material from which the material the layer 16 is made, and the pressure 120 applied by the pressurized region 24 of the chamber 14. The wall 26 maintains the pressure region 24 with fluid therein. In one embodiment, the fluid is air. In other embodiments, liquid fluids may be used. The perimeter layer 18 is secured by the clamping mechanism 80 selected from one of the embodiments of FIGS. 2–5, or a functional equivalent thereof.

A normal force 122 corresponds to the pressure 120 and urges the perimeter layer 18 against the base layer 16 and the drum 12. If a separate interface layer 20 exists between the base layer 16 and the perimeter layer 18, the pressure layer 120 and thus the normal force 122 is transmitted therethrough.

Figure 9A:
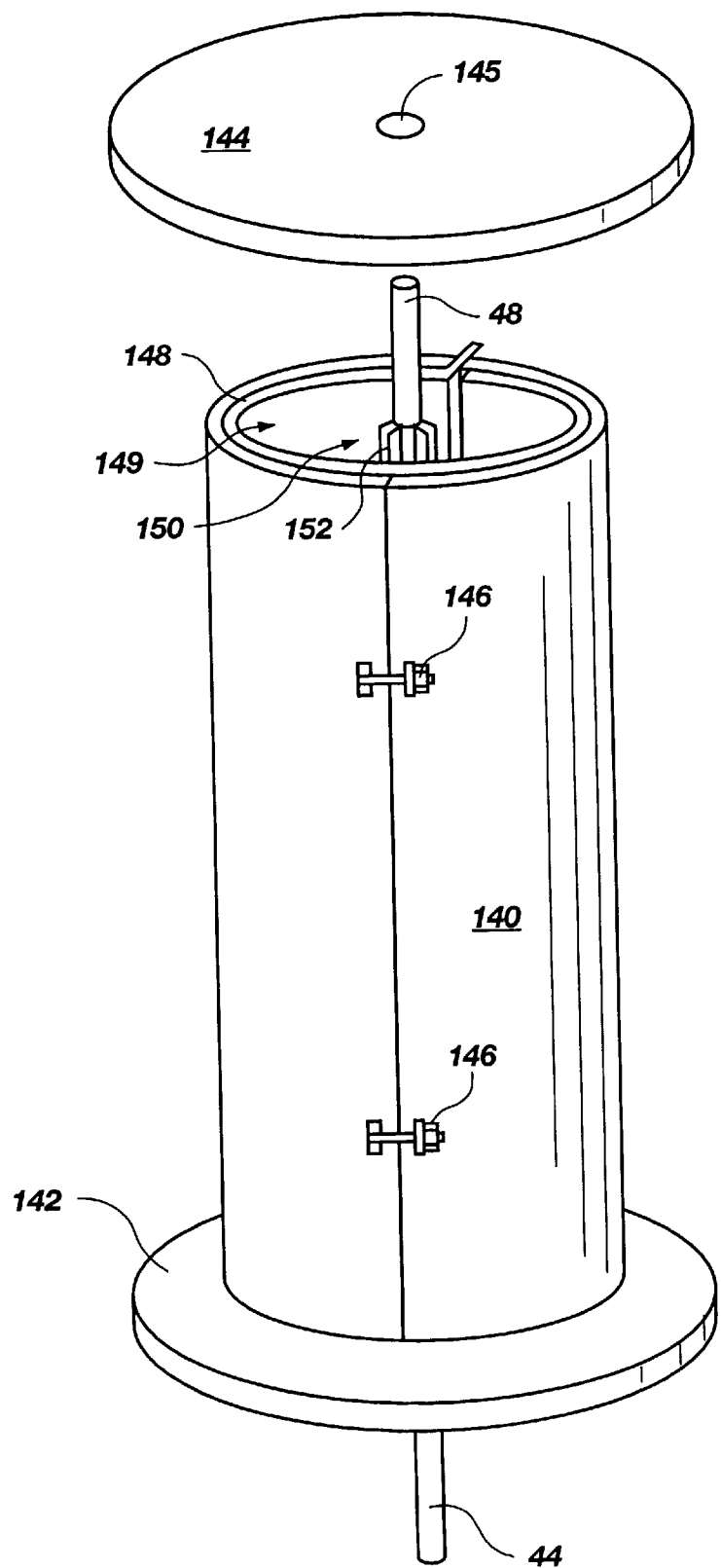
FIG. 9A is a schematic, perspective, partially exploded view of one embodiment of an apparatus for preparing soils to be tested as the central materials in an apparatus in accordance with the invention.
Figure 9B:
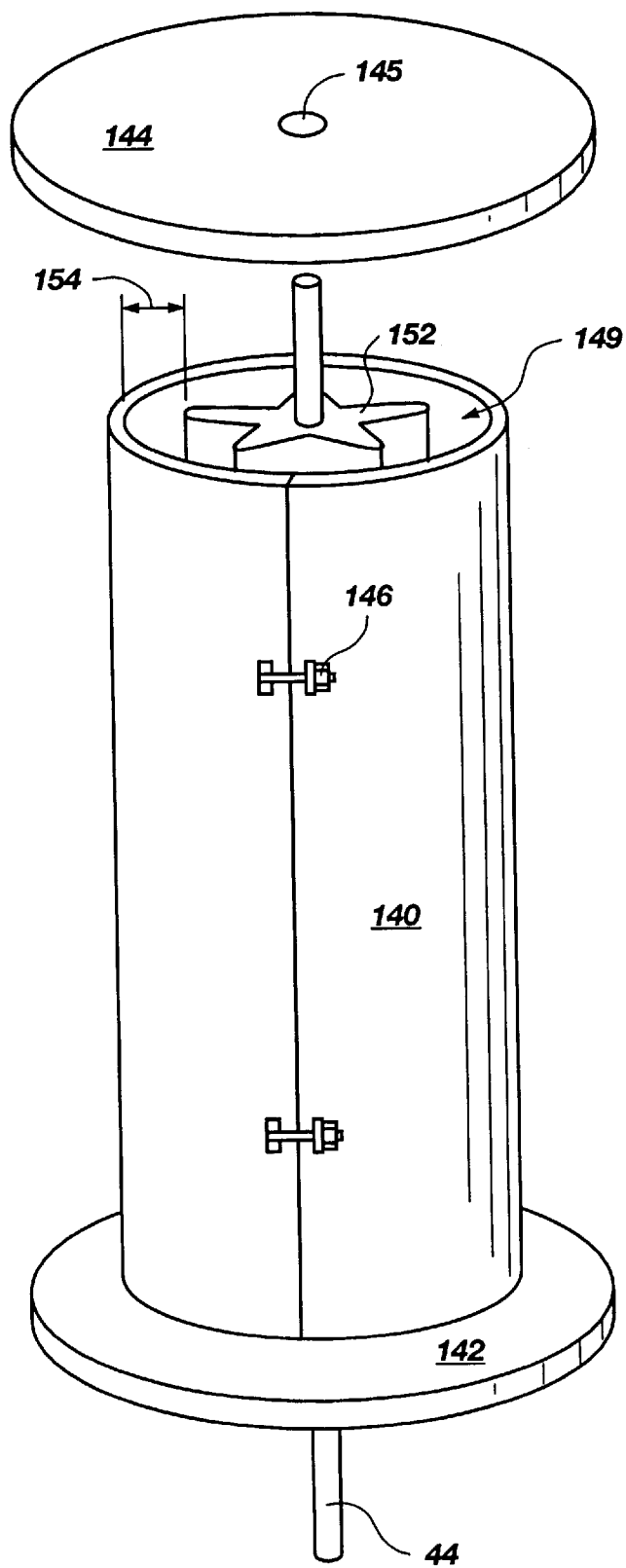
FIG. 9B is a schematic, perspective, partially-exploded view of the apparatus of FIG. 9A, illustrating an unlined mold and an oversized, fluted (vaned) mandrel.

Referring to FIGS. 9a–9b, a mold 140 may form a cylinder 12 or drum 12 of a geotechnical, naturally occurring material. In general, a base plate 142 may substitute for, or serve as a turn tape 116 or base 46. A top plate 144 may seal the mold 140 and maintain the shape of the material therein.

In one embodiment, an aperture 145 may receive the shaft 48 therethrough. In general, the shaft 44 may be contiguous with, or identical to the shaft 48. In general, the mold 140 is removed and the resulting drum 12 is placed in the chamber 14 for testing. In one embodiment, fasteners 146 may secure parting lines of a mold 140. A liner 148 may contact the mold 140, providing a testing material as well as containment for a less cohesive material forming the drum 12. In general, the liner 148 may be used in conjunction with the drum 12, the frame 17, and thus the perimeter layer 18 (e.g. as the perimeter layer 18 or in contact therewith), or may be free standing as an interface layer 20 between a drum 12 of a soil, and a perimeter layer 18.

When the drum 12 is formed of a soil material, a cavity 148 is filled with a soil sample and compacted around a mandrel 150. The mandrel 150 includes multiple flutes 152 or vanes 152 protruding radially therefrom. Depending on the nature of the soil in the cavity 149 the flutes may be comparatively long or short in a radial direction. In the embodiment of 9a, the vanes 152 are comparatively small. In the embodiment of FIG. 9b, the clearance 154 between the vanes 152 and the mold 140 is comparatively smaller. The clearance 154 is important in providing the performance of interest of a soil sample of the drum 12.

Figure 10:
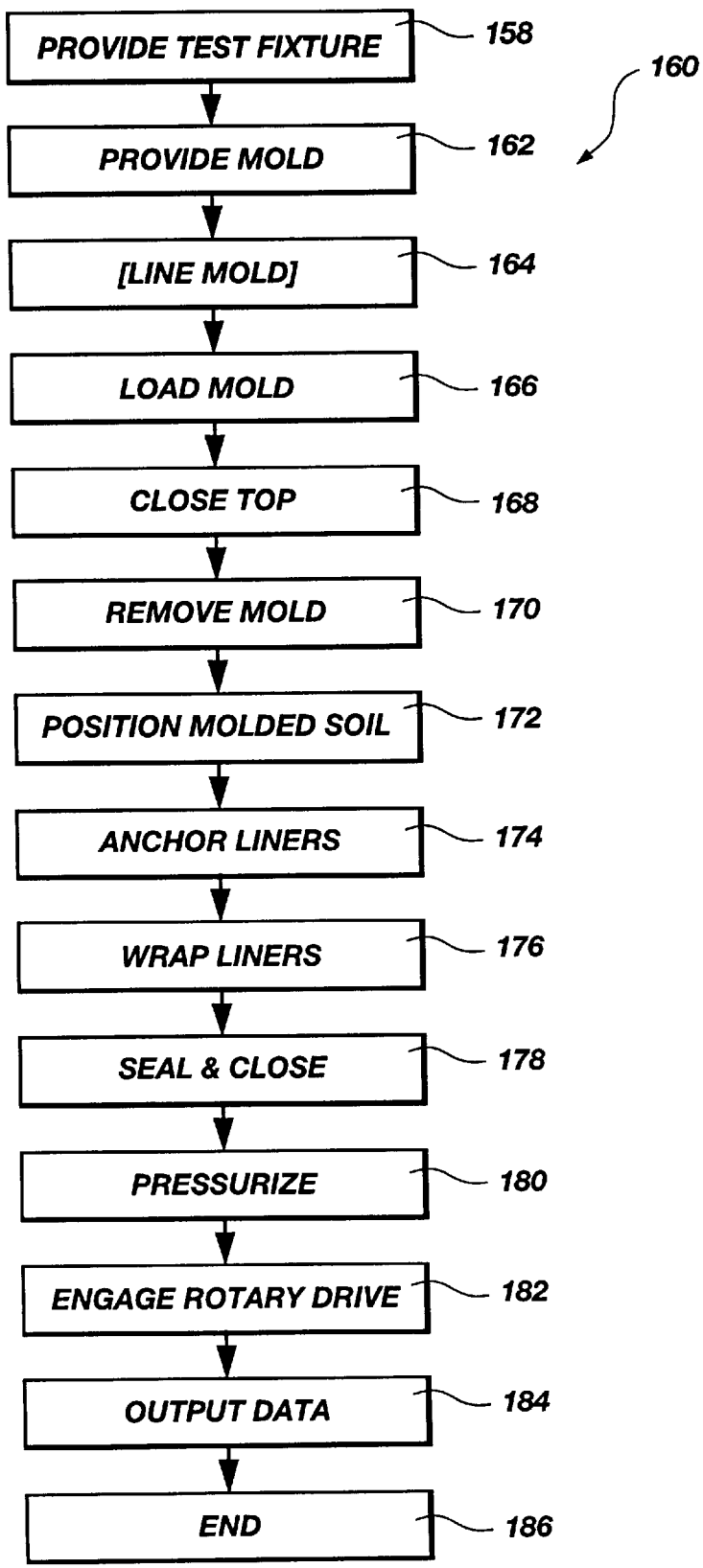
FIG. 10 is a schematic block diagram of a process in accordance with the invention.

Referring to FIG. 10, providing 158 a fixture 10 is an important part of a method 160 for testing geosynthetic and naturally occurring geotechnical materials. A provide step 158 may include building, setting up, or otherwise arranging the apparatus described with respect to FIGS. 1–9. The provide mold step 162 may be associated with the apparatus and procedures described with respect to FIGS. 9a–9b.

In general, a line step 164 including lining 164 a mold 140, is optional. In certain embodiments a geotechnical naturally occurring material will not necessarily be cohesive. Accordingly, lining 164 the mold 140 may be required in order to maintain a test sample having sufficient structural integrity to be handled and positioned within the apparatus 10. A load step 166 involves placing a soil sample in the mold 140, typically, the load step 166 involves layering and tamping the material to a desired density as per a universally acknowledged standard. For example, ASTM D 698, and ASTM D-1557, ASTM D-4253, and ASTM D-4254 standards provide methods for compacting soils using compaction, vibration, and so forth. The material protruding above the mold 140 at the location that the top plate 144 must fit, is removed.

The close step 168 involves closing the mold 140 using the top plate 144. Time may or may not be important with respect to the molded sample now forming a drum 12. Thus, a weight may be used. Nevertheless, in general, a weight is not substantial nor required. A remove step 170 requires opening the fasteners 146 to remove the mold 140 itself. The tables 142, 144 may remain. In certain methods 160 an apparatus 10, the plates 142, 144 may be removed and replaced with other plates in the apparatus 10. Nevertheless, in one presently preferred embodiment, the plates 142, 144 correspond directly to the plates or tables 46, 52 in the apparatus 10 of FIG. 1. Positioning 172 to the molded soil forming a drum 12 in the apparatus 10 may involve positioning the shaft 44, 48. For example, in one presently preferred embodiment, the shafts 44, 48 are inherent in the drum 12 of soil, and are used to position the entire sample (e.g. drum of soil) within the apparatus 10.

An anchor step 174 may be optional. In general, a liner 148 around a drum 12 of soil in a mold 140 may be the material to be tested. In an alternative embodiment, the liner 148 may be anchored as the perimeter layer 18. Thus, the liner 148 may serve as either the base layer 16, or the perimeter layer 18, or as an independent interface layer 20 therebetween.

The wrap step 176 for wrapping additional liners or layers within the apparatus 10, may lead or follow the anchor step 174. As a practical matter, sometimes anchoring 174 is easily done after wrapping 176. In other circumstances, anchoring 174 should precede the wrapping step 176.

The sealing and closing step 178 may include sealing the walls 37, 68 with the membrane 28 as well as sealing the wall 26 with respect to the supporting structure 30 and super structure 32 in order to form the chamber 14 in a sealed relation.

The pressurized step involves opening a valve 72 for venting the drum region, and opening the valve 76 to introduce fluid into the pressurizing region 24. The pressurize step 180 is effectively a loading step applying pressure to a membrane 28, and from a membrane 28 to the stackup 22 of layer 16, 18, 20 that may be disposed against the drum 12.

The engage step 182 involves operating the drive 38 for rotating the shaft 44, tables 46, 52, and the drum 12 therewith. As discussed above, the engage step 182 may rotate the frame 17 instead. Nevertheless, as a practical matter, it is much simpler to rotate the inner most members, such as the drum 12, rather than the frame 17.

The output step 184 provides data from the sensors 50 or sensor suite 50 identifying the torques, loads, forces, pressures, etc. that apply, as well as the displacements, angular velocities, and so forth corresponding to a particular method 160 or test 160 operating in the fixture 10. Individual steps within the process 160 may be repeated. Nevertheless, after sufficient data had been accumulated, an end step 186 may terminate the test for tearing down the samples and preparing the apparatus 10 for execution of another process 160.

Figure 11:
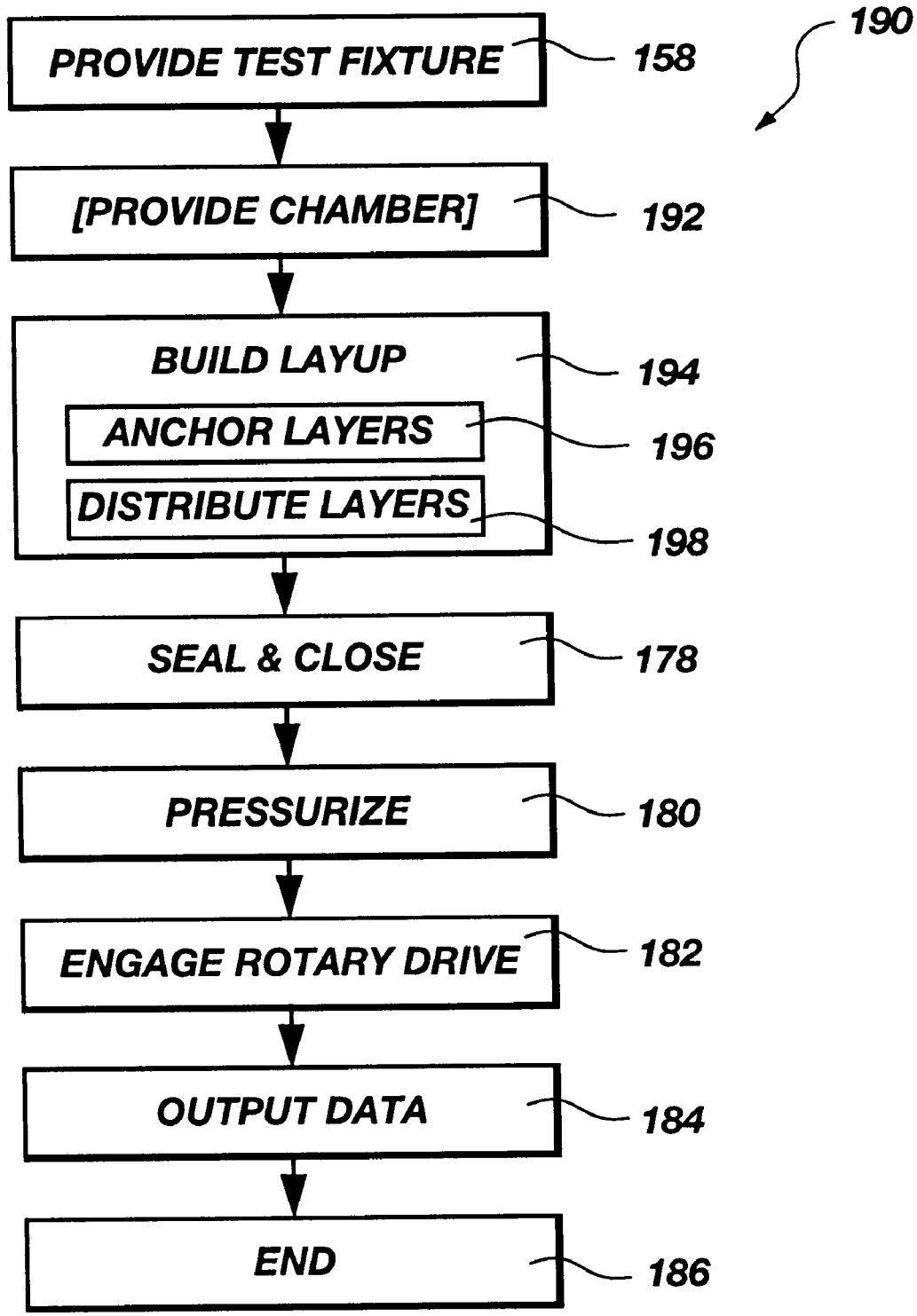
FIG. 11 is a schematic block diagram of a process for testing geosynthetic and geotechnical soil materials in accordance with the invention.

Referring to FIG. 11, a method 190 for testing geotechnical materials, both naturally occurring and geosynthetics, relies on rotational motion, rather than a linear motion. In general, the method 190 may be practiced with a fixture 10 such as the apparatus 10 of FIGS. 1–9. In general, the overall width 70 of the sample 70 may be selected to correspond with an applicable ASTM standard. For example, a standard width of approximately 12 inches or 0.3 meters has been successfully used to provide effective information. An overall circumference or length of a sample layer 16, 18, 20 may be from about 12 inches to about 30 inches or more. Nevertheless, in one presently preferred embodiment, a 12.9 inch circumference (corresponding to a 4 inch diameter drum) or 12.9 inch displacement in a circumferential direction has been found suitable.

The process 190 may begin with a provide step 158 for providing a test fixture to include a drum 12 with the frame 17 and the stackup 22 of layers 16, 18, 20. The provide step 192 includes providing a chamber 14. The provide step 192 may be optional for two reasons. Initially, pressure may be provided by a mechanism other than the pressurizing chamber 14 and the pressure region 24. On the other hand, the provide step 158 may involve providing the entire fixture 10 including both the chamber 14 and the drum 12 and all appurtenance thereto.

A build step 194 or layer step 194 provides the stackup 22 of layers 16, 18, 20 a portion thereof, or multiples thereof, as described in conjunction with FIGS. 1–9, and more particularly FIGS. 1 and 6. The build up step 194 may involve anchoring 196 selected layers 16, 18, 20 and the distribution or wrapping 198 step associated with those layers 16, 18, 20.

A seal step 178 may involve sealing and closing both the drum 12 and the membrane 28, as well as the chamber 14, in particular the wall 26, as described above. The sealing step 178 may involve certain cleaning and preparation of samples as described in conjunction with FIGS. 9a–9b.

A pressurize step 180 may involve opening the valve 76 to admit fluid through the conduit 78 into the pressurizing region 24. Similarly, the pressurize step 180 may involve relieving the bias of internal pressure within the drum 12 by opening the valve 72 in order to vent the cavity 73 through the conduit 74.

In one presently preferred embodiment, the pressurized step is entirely accomplished by fluid mechanics. In alternative embodiments, mechanical mechanisms may be used. In general, the pressurized step 180 may be thought of as providing a normal load for creating friction in response to motion in a rotating direction 90.

The engage step 182 involves engaging a drive mechanism 38 rotating the shafts 44, 48 connected to the drum 12. In general, the shaft 44 may rotate the drum 12 without slipping. Thus, as illustrated in FIG. 1, the drum 12 may be substantially fixed with respect to the shaft 44. In an alternative embodiment, such as those illustrated in FIGS. 9a–9b, a mandrel 150 containing a suitable array of vanes 152 may permit some amount of slipping, while countering slippage by moving the bulk of the material within the drum 12 in the rotating direction 90.

The output step 184 may provide the critical data of interest for use with the material properties. The output step 184 may involve integration or simply providing 184 the raw data from a suite of sensors. In general, parameters of interest may include material properties, which may be known in advance, or which may be tested. Likewise, other information to be output 184 may include all torques, forces, geometries, loads, effective coefficient of friction, power, velocities, displacements, and the like.

When the process 190 has been completed one or more times in conjunction with a testing protocol, the test may be ended 186.

Figure 12:
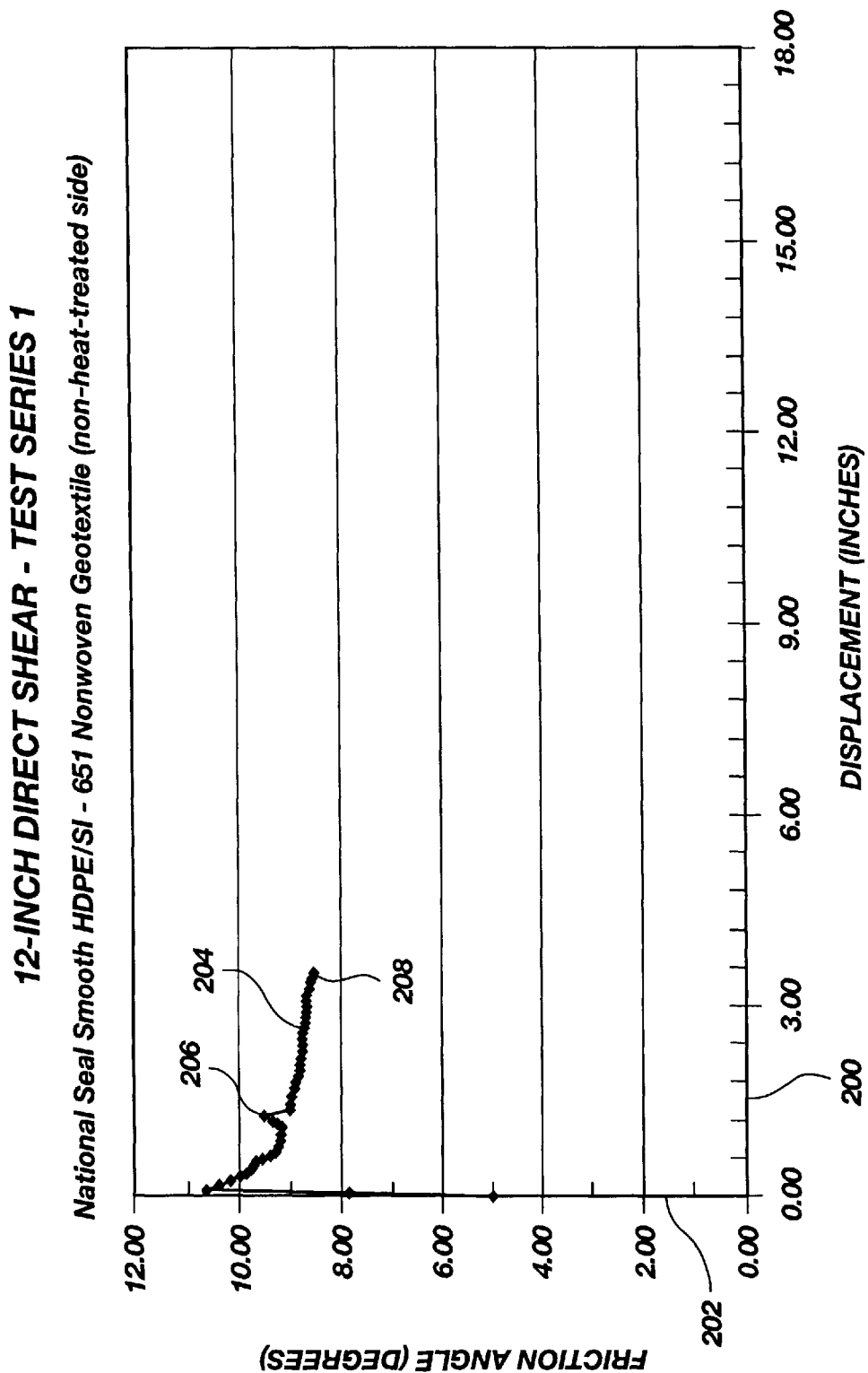
FIG. 12 is a chart illustrating sample data obtained in a test using a comparatively short displacement.
Figure 13:
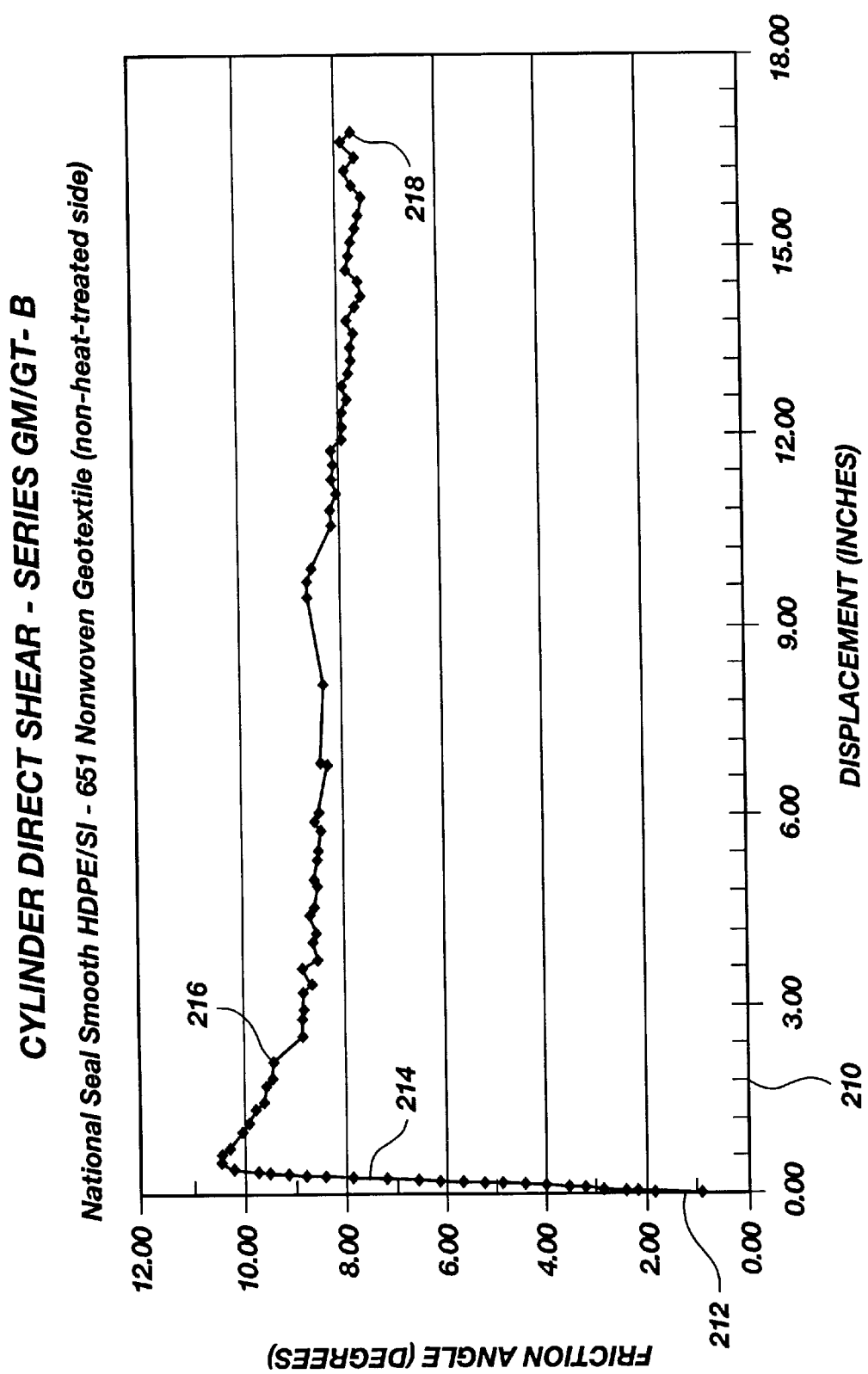
FIG. 13 is a chart illustrating data from testing with an apparatus and method in accordance with the invention.

Referring to FIGS. 12 and 13, a direct shear test result is provided for comparison. In the embodiment of FIG. 12, a displacement axis 200 corresponds to movement of one material against another in a friction test. The friction angle 202 or the axis 202 disposed orthogonally with respect to the displacement axis 200 reflects the friction coefficient. As a practical matter, the friction angle represents a consolidation of force, weight, friction coefficient, and the like. In the illustration of FIG. 12, the curve 204 is assembled from numerous individual data points 206. The end point 208 terminates at a displacement slightly beyond three inches.

One may note that the friction angle tolerable with the respective displacements 200 varies from about 10½ degrees to about 8½ degrees. Within the displacement of just over three inches, a friction angle 202 has decreased by this amount. Nevertheless, given the overall slope of the curve 204, projecting to displacements larger than several inches may be very risky. Being overly conservative, the slope of the curve 204 may be maintained. Risking any extrapolation that the slope of the curve 204 may asymptotically decrease or come to a zero value, is not justified by the data of FIG. 12.

Referring to FIG. 13, a displacement of approximately 16 inches in a sample is illustrated. The displacement axis 210 illustrates a total displacement within this test for the same material composition as the test of FIG. 12. Nevertheless, in this example, the maximum friction angle, as illustrated on the friction angle axis 212 varies from approximately 10½ degrees at displacements near zero to approximately 8½ degrees at a displacement 210 just greater than three inches.

Nevertheless, the individual points 216 making up the curve 214 continue to drop raggedly out to an end point 218. The end point 218 illustrates that indeed the slope of the curve 214 does change substantially after the three inches of displacement 210. Nevertheless, whereas the displacement between zero and approximately 3 inches resulted in a decay from 10½ to 8½ in the friction angle 212, the additional displacement to 16 inches results only in a decay of the friction angle 212 to a value of approximately 7½ or 7¾ degrees. Thus, a more aggressive design may be made, with a higher friction angle 212 than would be supposed by assuming the continuation of the steep slope of the curve 214 in the displacement region between zero and three inches.

An alternative anchoring system to fastening the leading edge of a geosynthetic is to hold it in place with a high friction surface. The high friction surface could be a "gripper plate" or gripper surface" mounted on the surface of the rotating drum, or a flexible yet inextensible gripper material wrapped around the outside of the samples (under the latex membrane) and fastened to the stationary anchor bar.

Composite geosynthetics, where one geosynthetic product is bonded to another material during manufacturing, are becoming more important and more common. A geocomposite has the advantages of shared properties. An example is heat bonding a smooth geomembrane to a geotextile in the factory in order to eliminate a potential slip plane between the geomembrane geotextile installed in the field. The internal shear strength of the composite can be tested in the Cylinder Direct Shear by anchoring one part of the composite to the rotating drum and the other part to the stationary anchor bar.

From the above discussion, it will be appreciated that the present invention provides a method and apparatus for providing substantially increased displacements for evaluation of effective coefficient of friction in shear between multiple layers of geotechnical materials (naturally occurring) and geosynthetic layers disposed thereon. As a practical matter, the effective coefficient of friction between materials in geotechnical installations is not constant with displacement. Moreover, conventional testing methods may lead to overly conservative design criteria, or extrapolation using improper constants of proportionality.

Accordingly, the apparatus and method in accordance with the invention provide reliable data of substantially larger displacements than conventional apparatus and methods. In one embodiment of an apparatus and method in accordance with the invention, multiple, cylindrical members may be positioned to displace tangentially (circumferentially) with respect to one another, while being loaded radially. An effective coefficient of friction may provide an improved determination for a friction angle on which a geosynthetic material may be disposed over a geotechnical field.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An apparatus comprising:
   a frame for supporting the apparatus;
   an axle effective to rotate with respect to the frame;
   a rotary member fixed to move with the axle in a rotary motion;
   a first geotechnical layer disposed on an outer surface of the rotary member to move in substantially fixed relation therewith in the rotary motion;
   a rack fixed with respect to the frame and disposed to extend circumferentially with respect to the rotary member, the rack comprising securement members for securing a geotechnical material thereto;
   a loading member positioned to be effective to apply a load in a normal direction urging the rotary member and the rack into frictional relation in response to tangential forces arising from the load therebetween;
   a sensor mechanism operably engaged with the rotary member for recording displacement thereof with respect to the frame;
   a pressurizing chamber positioned proximate the rotary member and rack for supplying the load therebetween; and
   a motive member for providing power to the axle effective to rotate a rotary member.

2. The apparatus of claim 1, wherein the loading member comprises a membrane positioned in the pressure chamber, the membrane being effective to resist a fluid flow therethrough, and effective to transmit pressure from the pressure chamber to the loading member.

3. The apparatus of claim 2, further comprising a geosynthetic layer disposed to extend circumferentially along the rack, and being fixedly secured along at least one substantially axial expanse on the rack, to be effective to remain fixed with respect to the rack during operation of the apparatus.

4. The apparatus of claim 3, wherein the first geotechnical layer comprises a geosynthetic material disposed to extend axially a selected distance along the rotary member, and to extend circumferentially along a surface corresponding to the rotary member, the geosynthetic material being fixedly secured along a substantially axial dimension of the rotary member, to be effective to maintain a fixed relationship with respect to the rotary member.

5. The apparatus of claim 4 further comprising a fluid supply operably connected to the pressure chamber for pressurizing the pressure chamber for applying the load.

6. The apparatus of claim 5 further comprising a vent secured to the pressurizing chamber for relieving fluid trapped within the membrane on a surface of the geosynthetic material opposite a pressurized region of the pressure chamber.

7. The apparatus of claim 3 further comprising an interface layer disposed between the first geotechnical layer associated with the rotary member and the geosynthetic layer associated with the rack.

8. The apparatus of claim 7, wherein the interface layer comprises another geosynthetic layer.

9. The apparatus of claim 7, wherein the interface layer further comprises at least one geotechnical material naturally occurring.

10. The apparatus of claim 9 wherein the interface layer further comprises a second geotechnical material naturally occurring.

11. The apparatus of claim 10 wherein the interface layer further comprises another layer formed of an additional geosynthetic material.

12. The apparatus of claim 3, wherein the motive member comprises a motor and transmission effective to rotate the rotary member at an angular velocity effective to provide an effective, relative, linear velocity between the first geotechnical layer and the geosynthetic layer to be effective to provide an effective coefficient of friction in response to the load applied normally therebetween.

13. A method for testing materials, the method comprising:
   providing a fixture having a rotary member, driven by a rotary drive, and a fixed member, the rotary member being disposed to rotate with respect to the fixed member while experiencing a force directed in a radial direction to urge the rotary member and fixed member into close, proximity, and having an interface layer disposed to extend substantially between the rotary member and fixed member for testing the effective coefficient of friction between the fixed member and the rotary member as a function of intervening materials therebetween;
   providing a chamber for containing the fixture therein;
   providing a layer comprising a first material disposed on a surface of the rotary member;
   providing a second layer of a material selected and positioned with respect to the fixed member to remain in a tangentially, substantially fixed relation thereto;
   sealing the fixture inside the chamber;
   pressurizing the chamber to effectively urge the fixed member and the rotary member into closer proximity, capturing the first and second layers therebetween;
   engaging the rotary drive to rotate the rotary member with respect to the fixed member; and
   providing output data reflecting the rotational load required to drive the rotary member, the radial load urging the fixed member and the rotary member into closer proximity, and sufficient to determine a correlative relationship therebetween.

14. The method of claim 13 further comprising anchoring the layers along respective substantially axial paths with respect to the respective rotary member and fixed member, respectively.

15. The method of claim 14 further comprising distributing the layers to extend substantially completely in a circumferential direction about the rotary member and fixed member.

16. The method of claim 13 further comprising sealing the fixed member and rotary member within a membrane, and venting the region within the membrane to apply a force normal to an interface between the two layers.

17. The apparatus of claim 13, further comprising wrapping additional layers between the first and second layers.

18. The method of claim 17, further comprising disposing the third layer between the first and second layers and leaving the third layer to move independently from the rotary member and the fixed member.

19. The method of claim 13, further comprising positioning a molded, naturally occurring, geotechnical material as the rotary member.

20. The method of claim 13, further comprising positioning a molded, naturally occurring geotechnical material as the fixed member.

21. The method of claim 19, further comprising disposing a geosynthetic material along a diameter of the geotechnical material.

22. An apparatus comprising:
- a first member disposed to rotate a surface in a tangential direction, the surface extending tangentially in a circumferential direction and axially in a longitudinal direction;
- a fixed member extending axially in a longitudinal direction and extending circumferentially in a tangential direction, radially proximate the rotary member;
- a motive member operably connected to provide a torque to the rotary member for moving the rotary member with respect to the fixed member;
- a first material positioned to maintain a fixed relation with the stationary member, being positioned between the rotary member and the stationary member;
- a second material disposed to extend longitudinally and circumferentially along a surface of the rotary member, being positioned between the rotary member and the stationary member;
- at least one of the first material and the second material being selected from the group consisting of geotechnical materials and geosynthetic materials; and
- a data recording apparatus operably connected to detect a load corresponding to the torque applied by the motive member to the rotary member, the relative displacement between the rotary member and the stationary member, and a normal force urging the rotary member and the stationary member toward a closer proximity.

23. An apparatus comprising:
- a rotary member configured to secure a first material extending circumferentially and axially to move circumferentially therewith;
- a stationary member configured to secure a second material in fixed relation with respect thereto, the second material being positioned between the rotary member and the stationary member to extend axially and circumferentially;
- at least one of the first material and the second material being selected from the group consisting of geotechnical materials and geosynthetic materials;
- a motive member operably connected to move the rotary member with respect to the fixed member; and
- a sensor mechanism operably connected to reflect engagement between the first material and the second material.

24. The apparatus of claim 23, further comprising a loading member attached to apply a pressure load in a radial direction for urging the rotary member and the stationary member into frictional relation.

25. The apparatus of claim 24, further comprising a pressurizing chamber positioned proximate the rotary member and the stationary member for supplying the load therebetween.

26. The apparatus of claim 25, wherein the loading member comprises a membrane effective to resist a fluid flow therethrough, and configured to transmit pressure from the pressure chamber to the loading member.

27. The apparatus of claim 26, further comprising a fluid supply operably connected to the pressure chamber for pressurizing the pressure chamber.

28. The apparatus of claim 27, further comprising a vent secured to the pressure chamber for relieving fluid trapped within the membrane on a surface of the material opposite a pressurized region of the pressure chamber.

29. An apparatus comprising:
- a first member having axial, circumferential, and radial directions, and disposed to rotate in a circumferential direction about an axis extending in the axial direction adapted to draw therewith a first material to form a surface extending axially and circumferentially proximate the first member;
- a fixed member positioned radially proximate the first member and extending axially and circumferentially for securing a second material positioned between the rotary member and the stationary member to be proximate the fixed member and in substantially fixed relation with respect thereto;
- a motive member operably connected to move the first member with respect to the fixed member;
- at least one of the first material and the second material being selected from the group consisting of geotechnical materials and geosynthetic materials; and
- a data recording apparatus operably connected to detect a parameter reflecting engagement between the first and second materials.

30. The apparatus of claim 29, wherein the parameter is selected from the group consisting of a force, a torque, a relative angular displacement between the rotary member and the stationary member, a relative linear displacement between a first location in the first material and a second location in the second material, a relative angular displacement between the first location in the first material and the second location in the second material; a normal force urging the first and second materials radially together, and a normal pressure urging the first and second material radially together.

* * * * *